(12) United States Patent
Metelski

(10) Patent No.: US 6,539,333 B1
(45) Date of Patent: Mar. 25, 2003

(54) STAND HAVING AN AUTOMATIC BALANCING DEVICE

(75) Inventor: Andrzej Metelski, Romanshorn (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 10/183,263

(22) Filed: Jun. 27, 2002

(30) Foreign Application Priority Data

Jan. 4, 2002 (DE) .......................... 202 00 079

(51) Int. Cl.⁷ .............................. G06F 15/02
(52) U.S. Cl. .................................... 702/173
(58) Field of Search ................... 702/173, 175; 73/788; 248/123, 123.11, 127, 125.7; 359/382, 384; 901/8

(56) References Cited

U.S. PATENT DOCUMENTS

| | | | | |
|---|---|---|---|---|
| 5,253,832 A | * | 10/1993 | Bolas et al. | 248/123.11 |
| 5,397,323 A | * | 3/1995 | Taylor et al. | 606/130 |
| 5,528,417 A | * | 6/1996 | Nakamura | 359/384 |
| 6,070,839 A | * | 6/2000 | Brenner et al. | 248/123.11 |
| 6,471,165 B2 | * | 10/2002 | Twisselmann | 248/123.11 |

FOREIGN PATENT DOCUMENTS

| | | |
|---|---|---|
| DE | 20019106 U1 | 3/2001 |
| DE | 20019109 U1 | 3/2001 |
| DE | 20019105 U1 | 6/2001 |
| DE | 4320443 C2 | 8/2001 |

OTHER PUBLICATIONS

Leica OHS–1 Leica Microsystems—the board for outstanding product no date.

* cited by examiner

*Primary Examiner*—Kamini Shah
(74) *Attorney, Agent, or Firm*—Hodgson Russ LLP

(57) ABSTRACT

The invention concerns a stand comprising an automatic balancing device in which an electric motor (5), an effective lever arm (h) is (automatically) modified by displacement of a counterweight (AG), independently of any static sensing of an imbalance. During the displacement of the counterweight (AG) (modification of effective lever arm h), the equilibrium state (balance state) is sensed dynamically by a measurement sensor (10) of a sensor (8), and is corrected in accordance with diagrams (software programs in a microprocessor (12) that activates the electric motor (5)). In this context, provision can be made for fast and slow operating modes for the electric motor (5), threshold values in the measurement signal, stops, and limit switches.

20 Claims, 3 Drawing Sheets

STAND HAVING AN AUTOMATIC BALANCING DEVICE

CROSS REFERENCES TO RELATED APPLICATIONS

This application claims priority of the German utility model application 202 00 079.6 which is incorporated by reference herein.

FIELD OF THE INVENTION

The invention concerns a stand having an automatic balancing device. In the field of surgical microscopes in particular, increasing use is being made of stands that balance out the weight of the microscope by means of an automatic balancing device. In this context, counterweights are displaced as a function of forces or moments that result from an imbalance, so that the load (microscope and its accessories) and the counterweights end up in a balanced-out state. This state is achieved when a user can move the microscope on the stand in three dimensions as if it were weightless. Brakes that lock the stand in a selected position in three dimensions are also, as a rule, provided in addition to the automatic balancing device.

BACKGROUND OF THE INVENTION

Conventional stands are braked during the automatic balancing process by means of at least one of the brakes. The imbalance is then measured (by measuring e.g. flexural, rotational, or inflection moments or forces). A computer then ascertains, for example with reference to a table, whether the stand is in balance or imbalance. If the stand is in imbalance, an adjustment command is generated for an adjustment motor, which adjusts at least one of the counterweights in such a way that the imbalance becomes smaller. If necessary, this operation is repeated until the imbalance is reduced to a minimum.

Since the measurement of the imbalance is performed with the load and the counterweight in the braked, stationary state, this automatic balancing method is a static measurement and control method. The inventor therefore refers to the known balancing method as the "static balancing method."

Balancing methods are used, for example, in the OHS of Leica Microsystems (brochure no. 10M15010EN) and in the assemblage of DE 43 20 443 C2.

The inventor has recognized that the known systems are disadvantageous in the following ways:

a) The procedure of measurement, calculation, activation, and adjustment takes time. Users, however, would like to have immediate and complete balancing without having to allow time to elapse.

b) During stepwise resolution of the measurement, activation, and adjustment operation, in particular during repetition in multiple steps, in extreme cases a vibration that is unpleasantly perceptible, and can even have a negative influence on the measurement, can be generated in the stand.

c) To eliminate the problem set forth in b), the counterweight must be moved slowly; this aggravates the problem described in a).

SUMMARY OF THE INVENTION

It is thus the object of the invention to create an apparatus which eliminates the disadvantages cited, by the fact that the automatic balancing operation is to be accelerated and the time necessary therefor is reduced, and by the fact that the stepwise resolution of the balancing operation is to be converted as much as possible into a continuous operation.

This object is achieved by modifying the conventional balancing device to create a "dynamic balancing operation" in which:

i) measurement of a static imbalance state is dispensed with;

ii) adjustment of the counterweight is performed continuously during balancing; and iii) during adjustment of the counterweight, the imbalance is measured dynamically as it changes.

iv) Comparison with tables, calculation of adjustment commands, etc. can be dispensed with. (Such operations can, however, also be provided for in dynamic balancing, although they do not constitute the basis of the system according to the present invention; they can in some circumstances serve merely to refine or improve the system. What is critical is that in the context of the invention, measurement occurs during adjustment and not with the stand in the static state.)

A new stand according to a described embodiment the present invention generally comprises an automatic balancing device in which a counterweight (AG) is displaceable on an effective lever arm (h) by an electric motor (5) and in which the electric motor (5) can be activated by means of a sensor (8) and microprocessor (12) via control lines (13), the microprocessor (12) executing a software program. The new stand is characterized in that the software program comprises program steps in which, as adjustment of the counterweight (AG) to modify the effective lever arm (h) is proceeding, the measured imbalance at the sensor (8) is ascertained, and the signal value thus dynamically measured is used for activation of the electric motor (5), the continuing adjustment motion of the electric motor (5) being influenced as necessary by the activation.

Further embodiments and developments of the invention are described herein.

The following improvements are achieved as a result of the new configuration of the stand with the new balancing philosophy, as described above:

Complete balancing of a stand is accomplished more quickly;

The system has less tendency to oscillate, and measurement results are more exact;

The new system requires less computer performance and is thus also less susceptible to malfunction;

As a result of the dynamic measurement and adjustment operation, the speed can be optimally adapted to the vibration behavior of the overall system. No abrupt stops occur during adjustment motion.

Although the text above and below refers to stands for surgical microscopes, the invention is nevertheless not limited thereto, but on the contrary is also available to other users of optical devices with stands and automatic balancing operations (e.g. telescopes, projectors, video and photographic cameras, etc.). The claims are thus to be construed correspondingly broadly.

The Parts List and the Figures, together with the subject matters described and protected in the Claims and the Utility Model applications referred to for the Applicant's MS-2, are an integral constituent of the disclosure of this Application.

BRIEF DESCRIPTION OF THE DRAWINGS

The Figures are described interconnectedly and in overlapping fashion. Identical reference characters denote identical components; reference characters having different indices indicate functionally identical components. Tables or diagrams are not necessarily scaled, and objects depicted are not necessarily at correct scale but are merely symbolic, since one skilled in the art can, with a knowledge of the invention, easily adapt existing assemblages in order to arrive at the solution according to the present invention.

In the drawings.

DETAILED DESCRIPTION OF THE INVENTION

Figure 1:
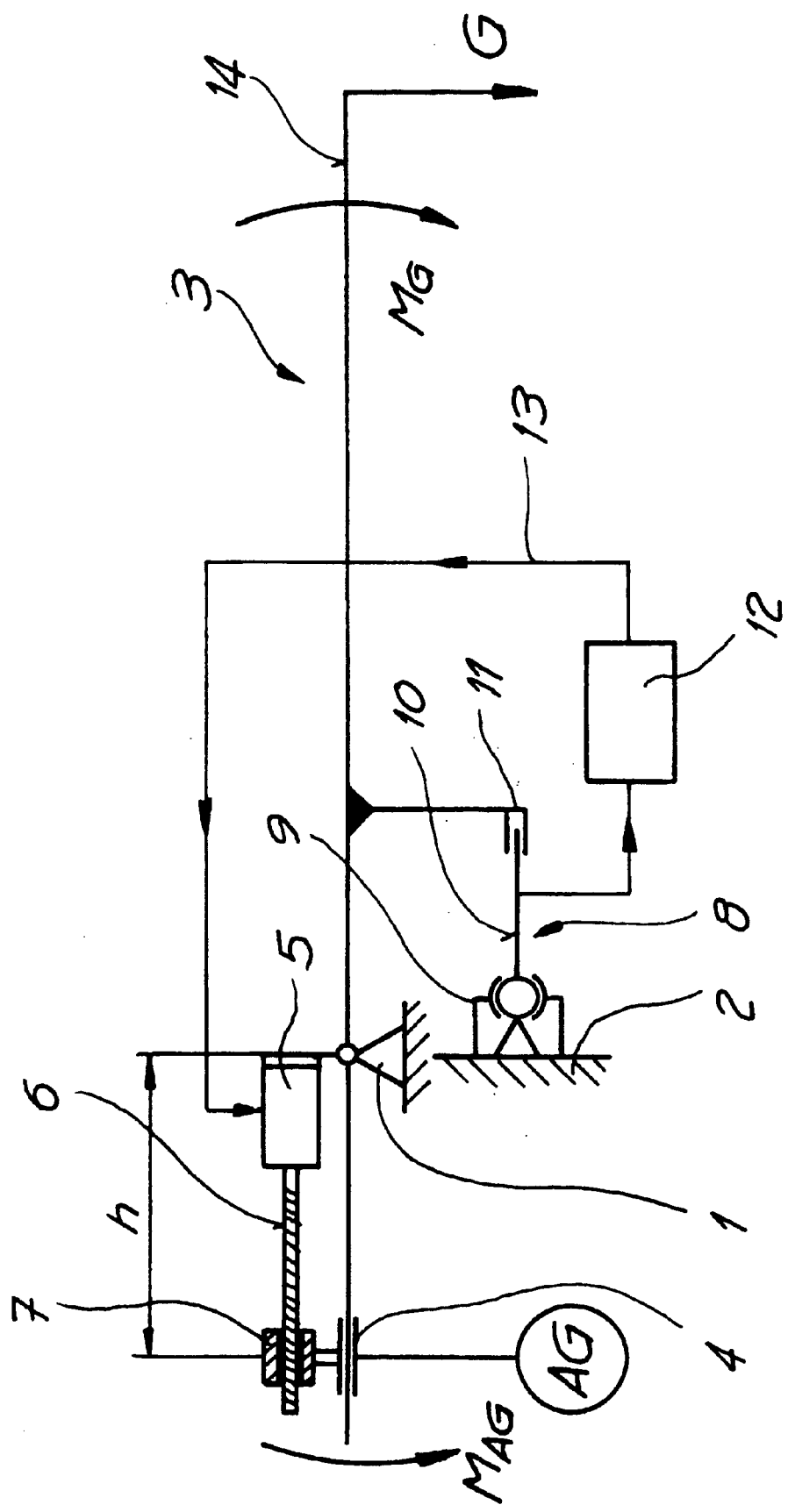
FIG. 1 shows a symbolic overall configuration of one possible stand assemblage.

As shown by the exemplary symbolic assemblage of FIG. 1, a stand balanced out in accordance with the present invention comprises a pivot bearing 1 that is fundamentally fixed in terms of position and location with respect to a column 2 (merely indicated) of the stand. The microscope or load G is suspended from an arm 14 of a double-arm support 3 that is mounted pivotably in pivot bearing 1. Located opposite load G on the other arm (effective lever arm h) of support 3 is a counterweight AG that is displaceable for balancing out purposes. It is suspended from a slider 4 that is mounted displaceably on support 3. An electric motor 5 that is mounted in stationary fashion on support 3 adjusts spacing h between counterweight AG and pivot bearing 1 via a spindle 6 that coacts with a nut 7. Nut 7 is rigidly joined to slider 4. The stand is balanced out when the tilting moment MG of the load is equal to the counterweight tilting moment MAG. During a displacement motion of the counterweight, a sensor 8 measures the magnitude of the respective imbalance.

Sensor 8 is constructed, for example, as follows: A measurement sensor 10 is mounted pivotably on column 2 and is braked with respect to column 2, during measurement, by a brake 9. A fork-shaped entraining element 11, which is immovably joined to support 3, creates an upward or downward load on the brake measurement sensor 10 in the event of imbalance (positive or negative imbalance). Measurement sensor 10 comprises a flexural sensor (not depicted) that is connected to a microprocessor 12. Microprocessor 12 controls electric motor 5 via a control line 13.

Also not depicted are an upper and a lower stop for measurement sensor 10, with which measurement sensor 10 comes into contact at the top or bottom in the event of an excessive imbalance, allowing no further measurement or deflection. In the state in which contact against the stop exists, the excess tilting moment MG or counterweight tilting moment (MG being not equal to MAG) generated by the imbalance is passed via the brake directly into column 2 and absorbed mechanically. Also not depicted in further detail is the fact that a locking system is provided that can be locked and unlocked manually in order to immobilize support 3 with column 2; this is for instances of large weight changes in the load, in order to reduce stress on sensor 8. As a result of this development, brake 9 can be made smaller.

Sensor 8 supplies a maximum positive signal upon contact against the upper stop, and a maximum negative signal upon contact against the lower stop. (This is a matter of definition and can also be selected the other way around.)

Figure 2:
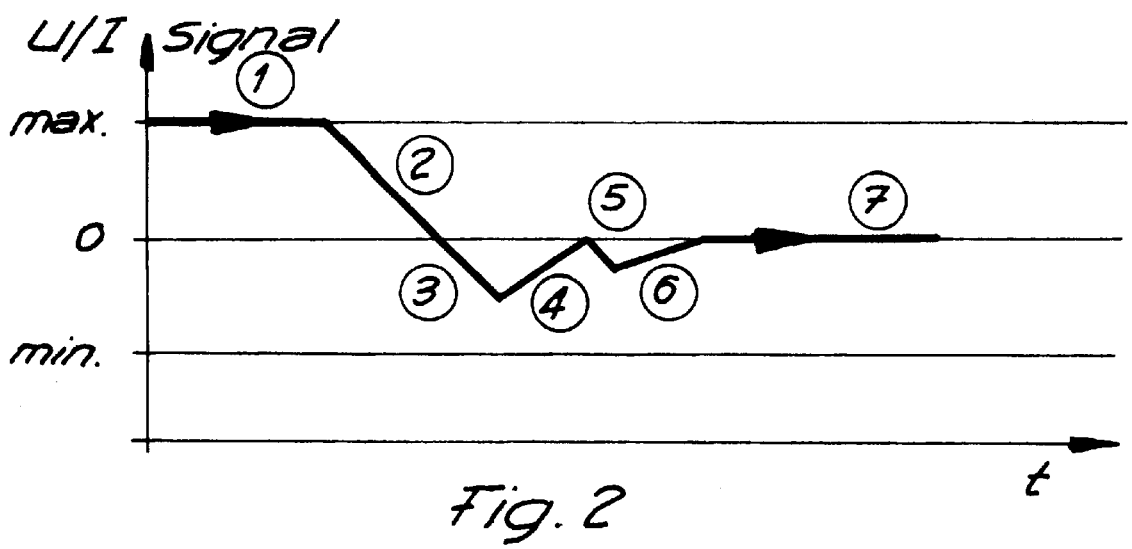
FIGS. 2 through 4 are symbolic diagrams that depict three different stepwise balancing procedures that measure on both sides of the "balanced" signal (zero signal) and shift the counterweight even beyond the balanced-out state.
Figure 3:
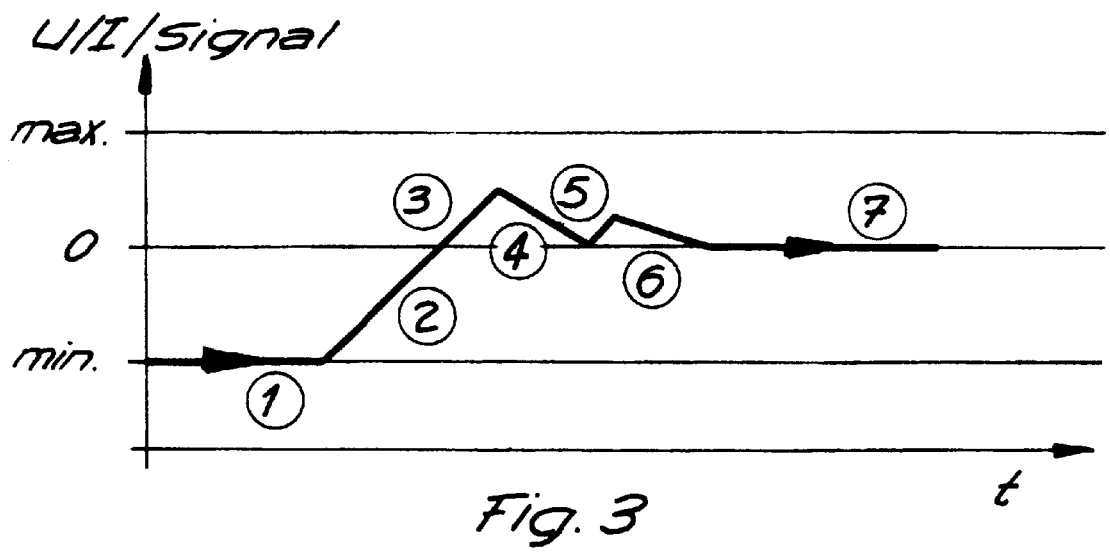
Figure 4:
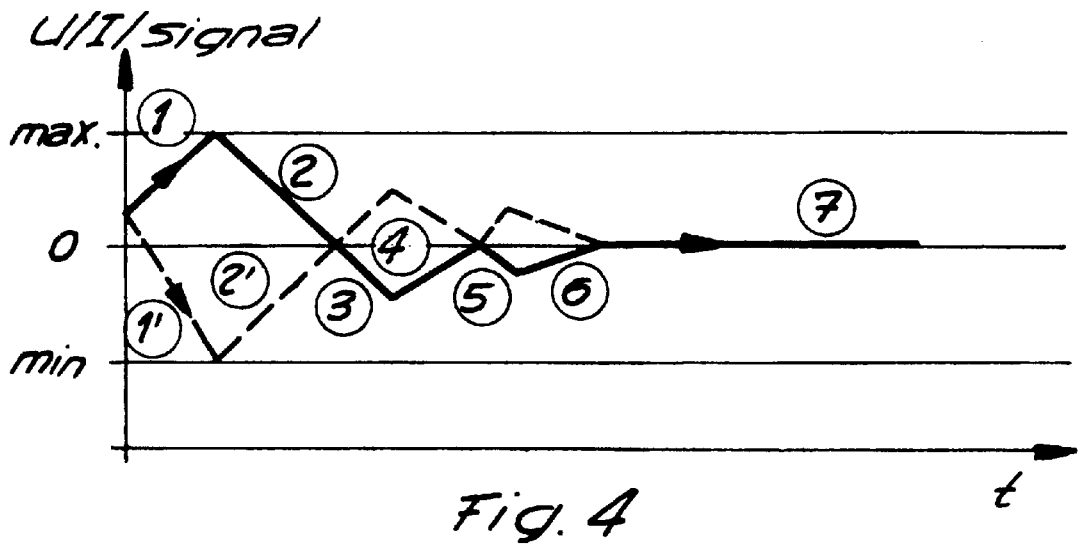

FIG. 2 shows a contact situation of this kind with positive imbalance and FIG. 3 shows a contact situation of this kind with negative imbalance, while FIG. 4 shows an imbalance that lies within a maximum positive or negative imbalance signal in which measurement sensor 10 is not resting against one of the stops, i.e. the imbalance is not so great.

Method of Operation when Balancing Out According to the Present Invention

The circled numbers 1 through 7 in the diagrams of FIGS. 2 through 4 indicate the steps of the balancing operation. In steps 1–2, fast advance of electric motor 5 occurs, in which counterweight AG is displaced as quickly as possible—in the negative direction, because it is in contact against the positive stop in the state shown in FIG. 2, and vice versa as shown in FIG. 3. The further adjustments of counterweight AG back in the positive direction then occur in slow advance (FIG. 2)—after crossing over the zero-signal line (signal in the balanced state)—or conversely in the negative direction (FIG. 3).

In contrast to the known situation, measurement occurs during the adjustment of counterweight AG, or measurement occurs after (and not before) counterweight AG has been set in motion. The motion direction of counterweight AG in the stopped state is determined from the actual stop at the positive or negative maximum. Because measurement also takes place in the dynamic state (while counterweight AG is moving), in this exemplary embodiment it may happen that the zero-signal line is crossed, as is evident between points 2 and 3. The adjustment of counterweight AG beyond the balanced state (zero signal) is provided so that balancing across the zero-signal line can be performed; in this exemplary embodiment, at least one change in the adjustment speed (deceleration) is brought about upon crossing the zero-signal line. If applicable, the speed change is accomplished continuously, specifically in a manner adapted to the oscillation behavior of the overall system. A speed change of this kind can be performed with each oscillation about the zero-signal line, although this is not necessary.

In the diagram of FIG. 4, the starting point of the balancing operation is not at a stop of measurement sensor 10 (at the edge of or outside the measurement range), but within the measurement range. Depending on the state of the system, in this case the adjustment of counterweight AG begins with a displacement in the positive direction (bold line), so that the imbalance is first increased even further (1) and from there, still in fast advance, displacement occurs in the negative direction (2) until the zero-signal line is crossed at (3) and a displacement reverse in slow advance occurs starting at (3), and optionally comes to a stop directly at the zero-signal line; or, as depicted, displacement continues in slow advance but over a smaller range, in order to enable fine adjustment and exact arrival at the zero-signal line (exact balance) (5, 6).

Also indicated in FIG. 4 with dashed lines is an alternative adjustment possibility in which counterweight AG begins to move in the other (negative) direction. with this variant it is conceivable that a displacement direction reversal command is issued as soon as the zero crossing occurs, so that in some circumstances the balanced state is achieved more quickly than with the variant described first.

In all the diagrams, the number of displacement motions is merely an example, so that it is clearly understood that depending on the fast operation and slow operation settings, and the inertia of the adjustment system having counterweight AG and electric motor 5, more or fewer displacement motions may be possible or necessary. In contrast to the known situation, what is essential is therefore not what is displaced when and where, but the fact that the balance is measured, and consequently the displacement motion is influenced or controlled, during the displacement.

The subject matter of the invention could thus also be stated as the fact that the adjustment motion of counterweight AG is accomplished inherently independently of the measurement, i.e. it is not that firstly something is measured and then something is adjusted, but rather that the adjustment proceeds and the result of the adjustment influences the further adjustment operation. The initial command for the movement direction in the positive or negative maximum region (at the stop) can be determined by the measurement software, but in particular also by limit switches. With such limit switches it is thus possible, in an undetermined balance state (measurement sensor at the stop), to prevent the adjustment motion from proceeding in the direction of further imbalance.

Figure 5:
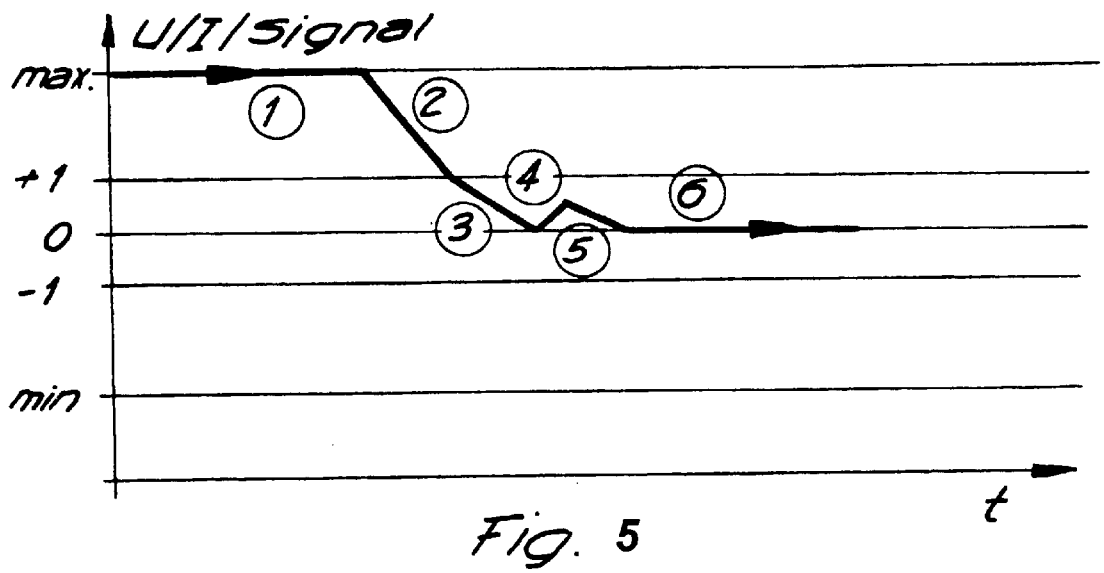
FIGS. 5 through 7 are symbolic diagrams that depict three different stepwise balancing runs which never cross the zero-signal line but always merely approach the balance state on one side of the zero signal (balanced state).
Figure 6:
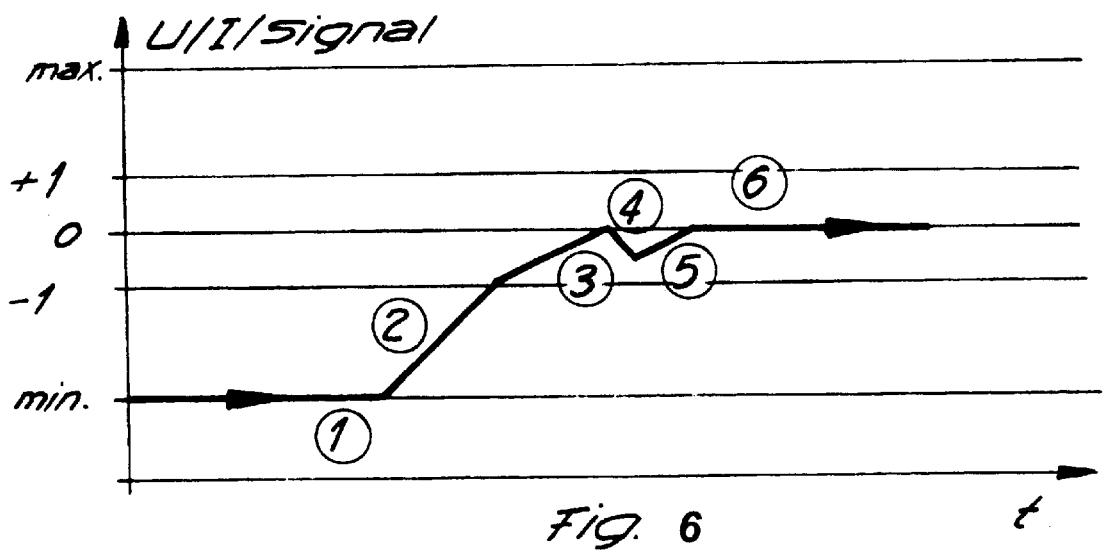
Figure 7:
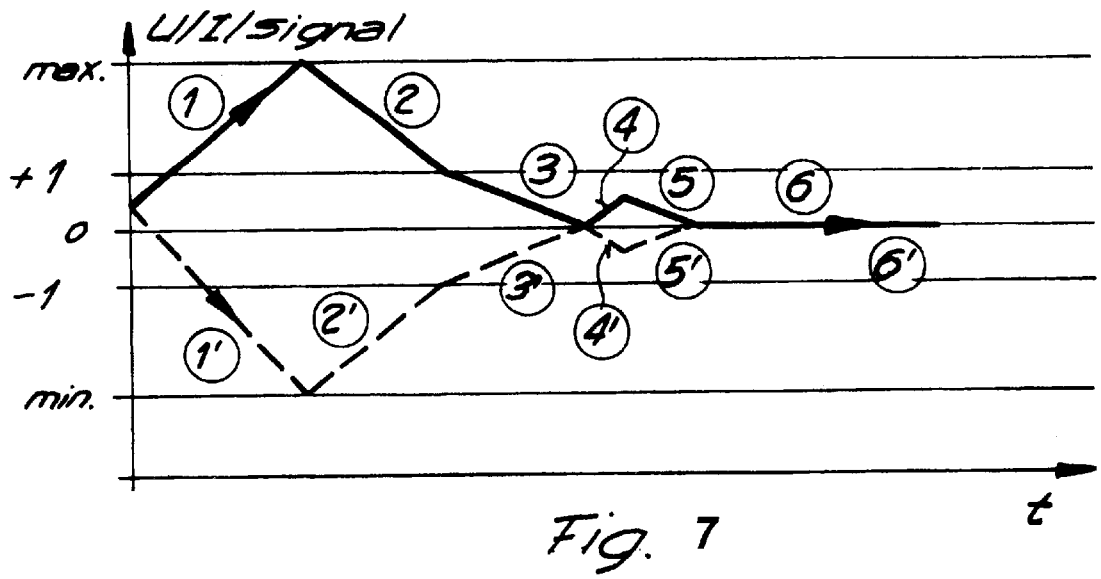

FIGS. 5 through 7 symbolically depict alternative balancing methods according to the present invention in which the zero line is never crossed during the adjustment of counterweight AG. The other features of the balancing method are the same, for example including the fast and slow operation modes. It is to be noted in this context that these two modes are cited by way of example, and that the method according to the present invention functions even without different speeds or with a larger number of different speeds.

Also indicated here symbolically and by way of example, differing from the methods according to the diagrams of FIGS. 2 through 4, are measurement ranges (between −1 and +1) entry into which automatically causes a switchover into slow operation mode. The methods according to FIGS. 5 through 7 are thus approximation methods triggered not by the zero line but by the −1 or +1 measurement region. In regions 1 and 2, a fast-advance adjustment of counterweight AG occurs; in regions 3 through 6, a slow-advance adjustment occurs.

In addition, FIG. 7 indicates by means of dashed curves a variant in which the balancing run is performed against the negative stop.

Summary Based on the Symbolic Illustration in FIG. 1

By means of electric motor 5, effective lever arm h is (automatically) modified by displacement of counterweight AG, independently of static sensing of an imbalance. During the movement of counterweight AG (modification of lever arm h), the equilibrium state (balance state) is sensed dynamically by means of a flexural sensor or the like (load cell) on measurement sensor 10 of sensor 8, and is corrected as shown in the diagrams (software programs in microprocessor 12), for example according to FIGS. 2 through 7. In this context, provision can be made for fast and slow operating modes for electric motor 5, threshold values in the measurement signal, stops, and limit switches.

The present invention is to be viewed in a complementary light by one skilled in the art who has consulted German Utility Models DE 20019109, DE 20019106, and DE 20019105, which (like the present Application) refer to a concretely embodied product ("MS-2") of the Applicant. German Utility Model DE 20019109 corresponds to European Patent Pub. No. 1205703 and U.S. patent application Ser. No. 10/010,103 filed Nov. 8, 2001, which is incorporated herein by reference. German Utility Model DE 20019106 corresponds to European Patent Pub. No. 1207336 and U.S. patent application Ser. No. 10/008,285 filed Nov. 8, 2001, which is incorporated herein by reference. German Utility Model DE 20019105 corresponds to European Patent Pub. No. 1207334 and U.S. patent application Ser. No. 10/010,101 filed Nov. 8, 2001, now which is incorporated herein by reference. In order to complement and better elucidate the concrete exemplary embodiment, the drawings of the aforesaid applications and the descriptions of the Figures thereof are considered to be also disclosed herein.

PARTS LIST

1 Pivot bearing
2 Column
3 Double arm support
4 Slider
5 Electric motor
6 Spindle
7 Nut
8 Sensor
9 Brake
10 Measurement sensor
11 Entraining element
12 Microprocessor
13 Control line
14 Load arm
h Effective lever arm
G Load (microscope)
AG Counterweight
MG Tilting moment of load
MAG Tilting moment of counterweight

What is claimed is:

1. A stand comprising:
an automatic balancing device including an effective lever arm (h), a counterweight (AG) displaceable on said effective lever arm (h), an electric motor (5) operable to displace said counterweight (AG) on said lever arm (h), a sensor (8) arranged to detect an imbalance in said stand, and a microprocessor (12) in communication with said sensor (8) and said electric motor (5) for activating said electric motor (5) according to a software program in response to said imbalance;
wherein said software program comprises program steps in which, while said counterweight (AG) is being displaced on said lever arm (h), the detected imbalance at said sensor (8) is ascertained and a signal value thus dynamically detected is used for activation of said electric motor (5), a continuing displacement of said counterweight (AG) by said electric motor (5) being influenced by said activation.

2. The stand as defined in claim 1, wherein said program steps comprise control commands that make the displacement of said counterweight (AG) performable at plurality of different speeds.

3. The stand as defined in claim 2, wherein said plurality of different speeds includes a fast speed and a slow speed.

4. The stand as defined in claim 2, wherein said control commands are issued to provide a counterweight displacement speed optimally adapted to the oscillation behavior of said stand and any load carried thereby.

5. The stand as defined in claim 2, wherein said control commands are issued such that an abrupt stop does not occur during the displacement of said counterweight (AG).

6. The stand as defined in claim 2, wherein said control commands are issued such that a transition between different counterweight displacement speeds is accomplished continuously.

7. The stand as defined in claim 2, wherein said program steps comprise control commands that enable displacement of said counterweight (AG) beyond a balanced state wherein said sensor (8) provides a zero-signal, whereby balancing across a zero-signal line can be performed.

8. The stand as defined in claim 7, wherein a change in the said displacement speed of said counterweight (AG) is brought about upon said signal value crossing said zero-signal line.

9. The stand as defined in claim 1, further comprising an upper stop and a lower stop respectively contacted by at least a portion of said sensor (8) incident to a corresponding positive or negative imbalance, whereby further differentiated imbalance detection is discontinued.

10. The stand as defined in claim 9, further comprising a pair of limit switches associated one with said upper stop and one with said lower stop, said pair of limit switches being connected to said microprocessor (12) to control an operating direction of said electric motor (5) and thus a displacement direction of said counterweight (AG).

11. The stand as defined in claim 1, further comprising:
 a column (2); and
 a load arm (14) for carrying a load (G), said load arm being mounted to said column.

12. The stand as defined in claim 11, wherein said sensor (8) comprises a measurement sensor (10) connected in brakable fashion via a brake to said column (2), and said measurement sensor (10) coacts with an entraining element (11) on said load arm (14).

13. The stand as defined in claim 11, wherein said load arm (14) and said lever arm (h) are configured on a double-arm support (3), said double-arm support (3) being pivotably mounted on said column (2) by a pivot bearing (1).

14. The stand as defined in claim 1, wherein said electric motor (5) comprises a spindle (6) that coacts with a nut (7) coupled to said counterweight (AG) for displacement therewith.

15. The stand as defined in claim 1, wherein said electric motor (5) is connected to a spindle/recirculating ball nut unit that engages into a slider (4) on said counterweight (AG).

16. The stand as defined in claim 11, wherein said load arm (14) is configured as a parallelogram linkage.

17. The stand as defined in claim 11, wherein said load arm (14) and said effective lever arm (h) are configured as a parallelogram linkage.

18. The stand as defined in claim 1, wherein said effective lever arm (h) is configured as a parallelogram linkage.

19. The stand as defined in claim 11, wherein said counterweight (AG) is joined via a force input slider to said effective lever arm, and is itself always held at a constant distance from said column (2).

20. The stand as defined in claim 13, further comprising a locking system that can be locked and unlocked manually in order to selectively immobilize said support (3) with respect to said column (2).

* * * * *